US00PP20995P3

(12) United States Plant Patent
Yosef et al.

(10) Patent No.: US PP20,995 P3
(45) Date of Patent: May 18, 2010

(54) STRAWBERRY PLANT NAMED 'SHAKED'

(50) Latin Name: *Fragaria ananassa*
Varietal Denomination: Shaked

(75) Inventors: Efraim Yosef, Derech Ramatim 71, P.O. Box 61 Hod HaSharon (IL) 45100; Asaf Meizles, Hod HaSharon (IL)

(73) Assignee: Efraim Yosef, Hod HaSharon (IL)

( * ) Notice: Subject to any disclaimer, the term of this patent is extended or adjusted under 35 U.S.C. 154(b) by 4 days.

(21) Appl. No.: 12/231,191

(22) Filed: Aug. 28, 2008

(65) Prior Publication Data

US 2010/0064399 P1 Mar. 11, 2010

(51) Int. Cl.
*A01H 5/00* (2006.01)

(52) U.S. Cl. ..... Plt./208
(58) Field of Classification Search ..... Plt./208, Plt./209
See application file for complete search history.

*Primary Examiner*—Susan B McCormick Ewoldt
(74) *Attorney, Agent, or Firm*—Michelle Bos

(57) ABSTRACT

This invention relates to a new and distinct variety of strawberry plant named 'Shaked'. 'Shaked' is primarily adapted to the climate and growing conditions of the Hod Hasharon, Sharon costal plain, Israel, and is primarily characterized by:

1. Excellent fruit flavor.
2. Conical fruit shape, dark red in color.
3. Firm juicy fruit.
4. Strong glossiness fruit.
5. Insertion of achenes above surface.
6. Production of many stolons.
7. Tolerance to anthracnose (*Colletotrichum acutatum*).

5 Drawing Sheets

Genus and species: *Fragaria ananassa.*
Variety denomination: 'Shaked'.

BACKGROUND OF THE INVENTION

The present invention relates to a new and distinct strawberry variety named 'Shaked'. The new strawberry 'Shaked' is a product of a planned breeding program conducted by the inventors at Hod Hasharon, Israel. The objective of the breeding program is to develop a new strawberry variety with quality fruits, high yield and tolerance to diseases. 'Shaked' is a result of a controlled cross made by the inventors in 2005 of female parent 'EF 14' (unpatented) and male parent 'EF 33' (unpatented). The parentage of 'EF 14' and 'EF 33' is unknown.

The new strawberry 'Shaked' was discovered and selected by the inventors as a single flowering plant within the progeny of the stated cross in a controlled environment in Hod Hasharon, Israel. After its selection, the new variety was asexually propagated by stolons and was extensively tested over the next several years in Hod Hasharon, Israel. This propagation has demonstrated that the combination of characteristics as herein disclosed for the new cultivar are firmly fixed and retained through successive generations of asexual reproduction.

BRIEF SUMMARY OF THE INVENTION

'Shaked' is primarily adapted to the climate and growing conditions of the Sharon coastal plain, Israel (32 degrees latitude) and to similar climatic regions. This region provides the needed growing conditions of autumn with high temperatures that promote primary plant growth and earliness of fruit production; and mild winter with moderate temperatures and many sunny days with low humidity, maintaining plant vigor and fruit quality during the production months.

The following traits have been repeatedly observed and are determined to be unique characteristics of 'Shaked', which in combination distinguish this strawberry plant as a new and distinct variety:

1. Excellent fruit flavor.
2. Conical fruit shape, dark red in color.
3. Firm juicy fruit.
4. Strong glossiness fruit.
5. Insertion of achenes above surface.
6. Production of many stolons.
7. Tolerance to anthracnose (*Colletotrichum acutatum*).

Plants of the new strawberry variety 'Shaked' differ from plants of the parents, 'EF 14' and 'EF 33' in the characteristics described in Table 1.

TABLE 1

| Characteristic | 'Shaked' | 'EF 14' | 'EF 33' |
|---|---|---|---|
| Fruit Size | Medium | Large | Medium |
| Insertion of achenes | Above surface | Level with surface | Above surface |
| Time of flowering | Regular | Late | Early |
| Firmness of the flesh | Medium | Firm | Medium |
| Plant size | Medium | Large | Small |
| Flavor | Excellent | Medium | Medium |
| Average number of stolons | Many | Few | Very many |
| Attitude of fruiting truss | Semi-erect | Semi-erect | Prostrate |

'Shaked' has been compared to the 'Yuval' variety (U.S. Plant Pat. No. 17,388) and has been found to be distinct therefrom. The fruit of 'Shaked' ripens later than that of 'Yuval', and is darker in color than 'Yuval'. 'Shaked' has also been compared to the 'Tamar' variety (U.S. Plant Pat. No. 11,135) and has been found to be distinct therefrom, in that the fruit of 'Shaked' is more firm than that of Tamar. In comparison with 'Rotemi' (pending U.S. Plant patent application Ser. No. 12/231,192), 'Shaked' has been found to produce more stolons than 'Rotemi'.

BRIEF DESCRIPTION OF THE PHOTOGRAPHS

The accompanying color photographs illustrate the overall appearance of typical specimens of the new strawberry variety 'Shaked', at various stages of development as true as it is reasonably possible with color reproductions of this type. Color in the photographs may differ slightly from the color value cited in the botanical description, which accurately describes the color of 'Shaked'. The depicted plant and plant parts of the new strawberry variety 'Shaked' were taken in Hod Hasharon, Israel, and are approximately 3 to 7 months old.

DETAILED BOTANICAL DESCRIPTION

Figure 1:
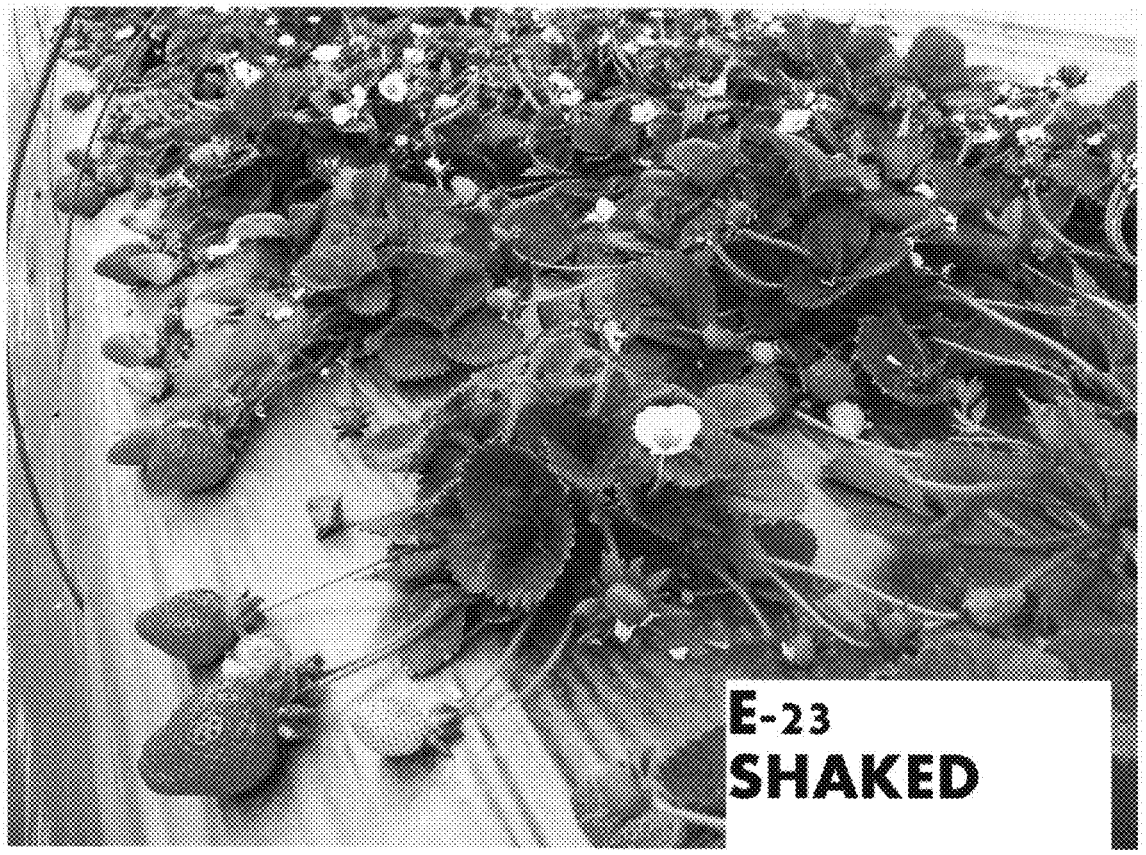
FIG. 1 shows typical fruiting field characteristics of 'Shaked' taken in the month of March 2008.
Figure 2:
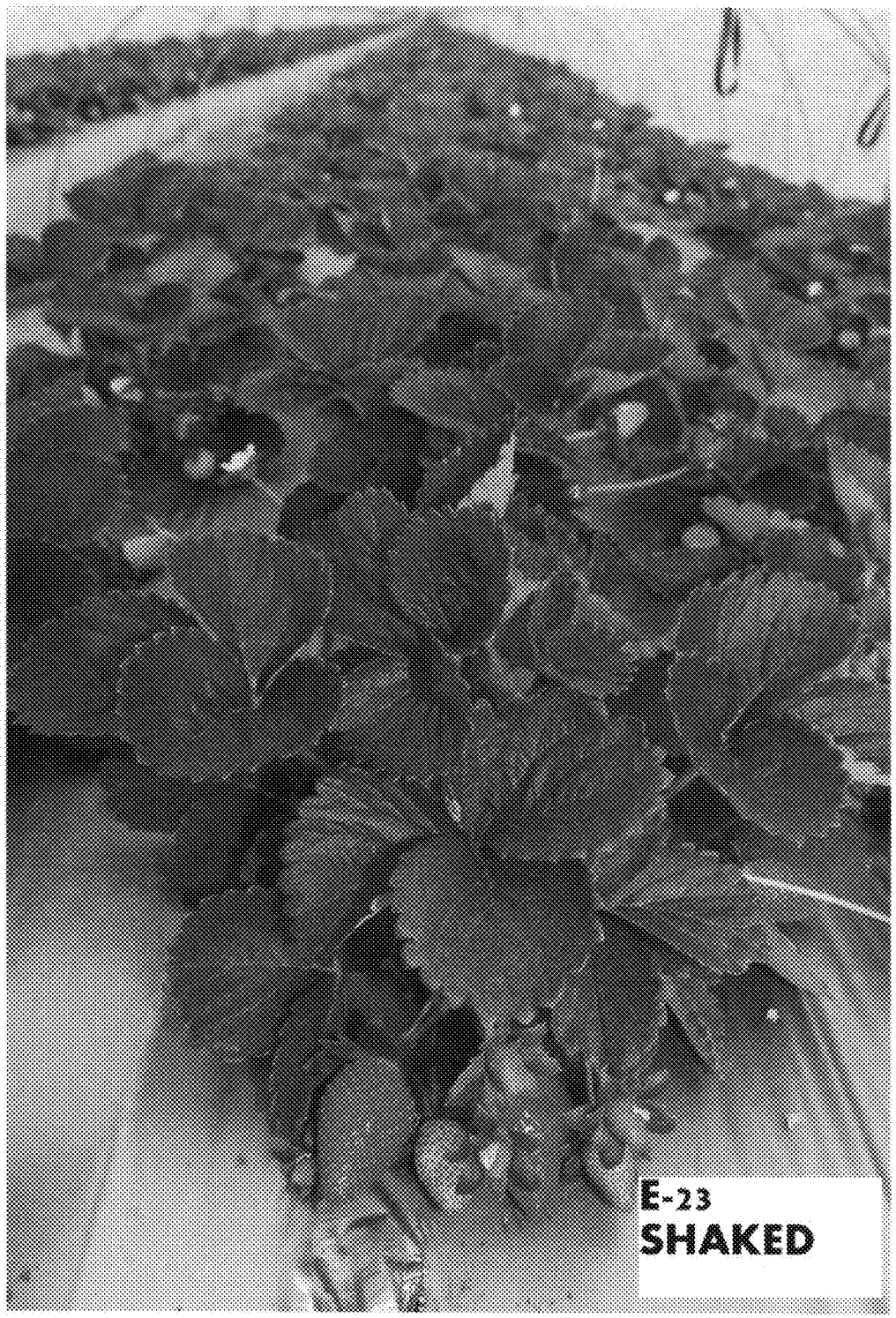
FIG. 2 shows a close-up view of a typical leaf structure of 'Shaked' taken in the month of December 2007.
Figure 3:
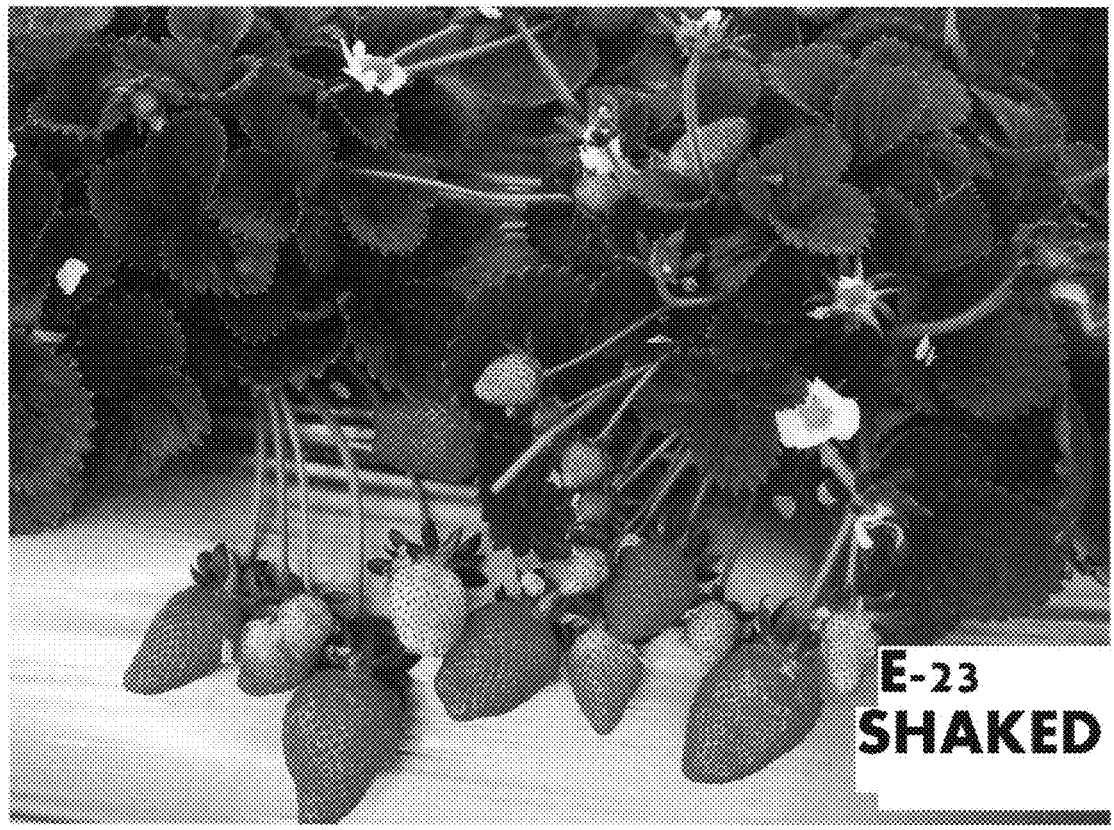
FIG. 3 shows typical mature and immature field fruit of 'Shaked' taken in the month of March 2008.
Figure 4:
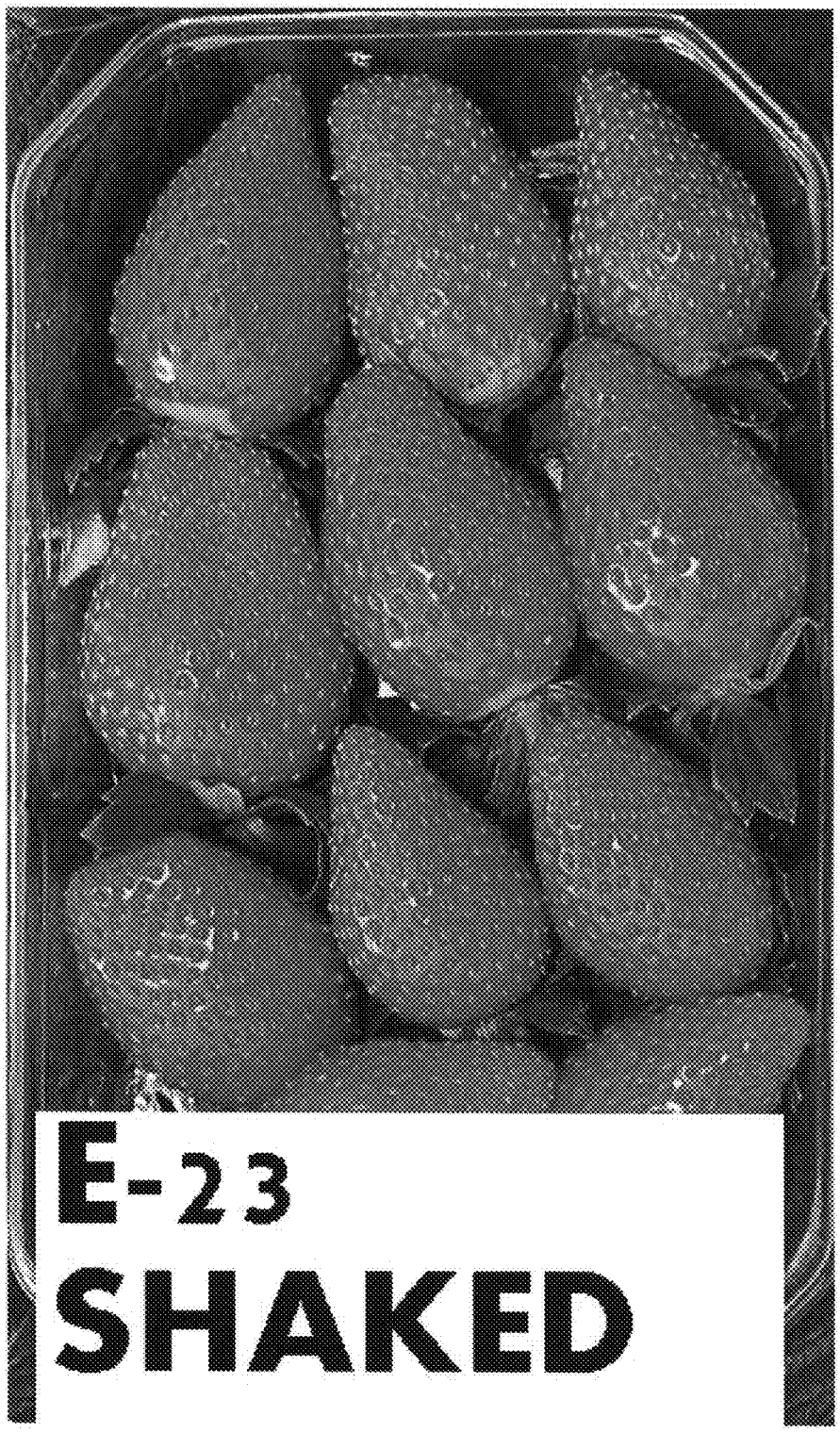
FIG. 4 shows a close-up view of mature fruit of 'Shaked' taken in the month of December 2007.
Figure 5:
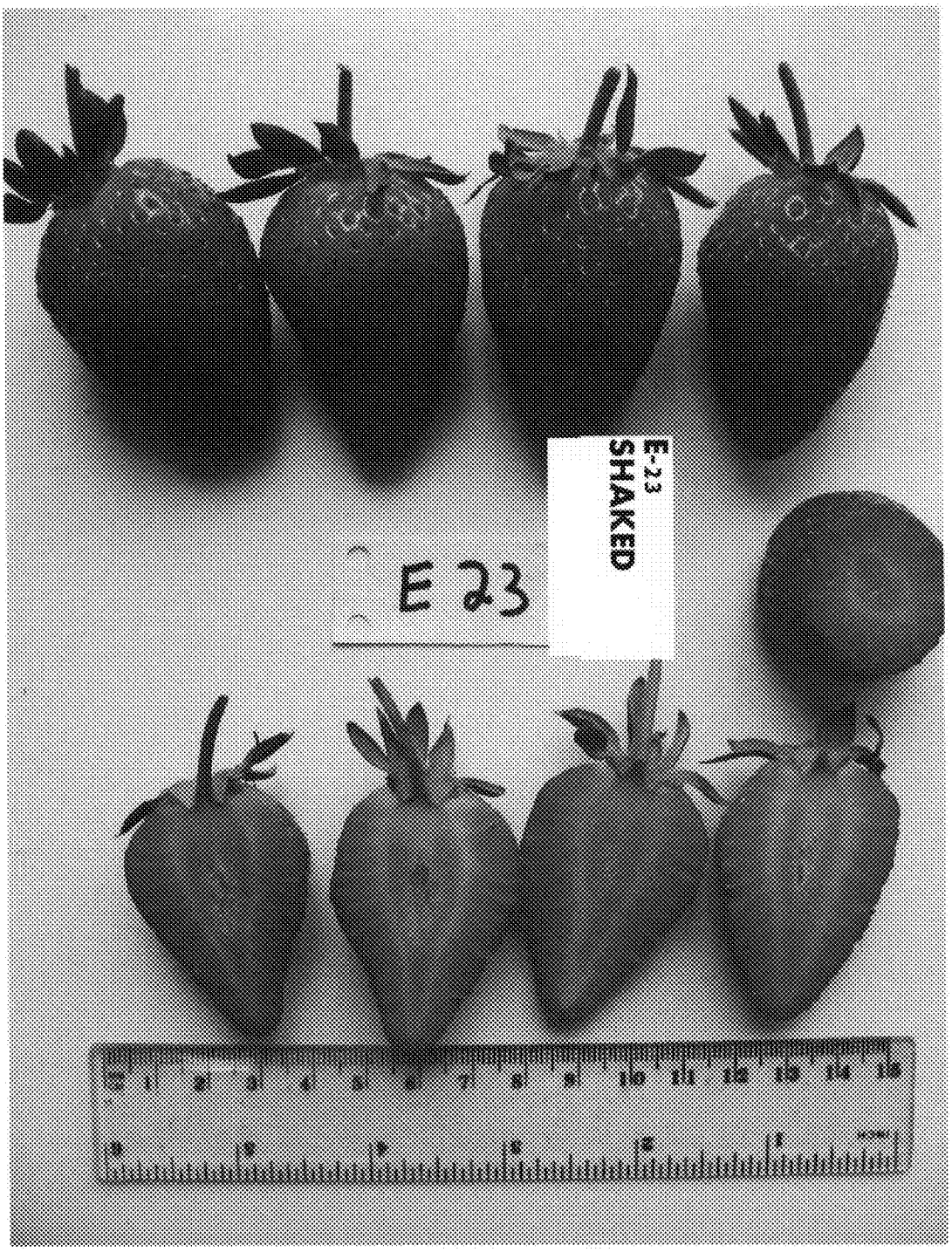
FIG. 5 shows typical internal and external mature fruit characteristics of 'Shaked' taken in the month of March 2008.

'Shaked' has not been observed under all possible environmental conditions. The characteristics of the new variety may vary in detail, depending upon variations in environmental factors, including weather (temperature, humidity and light intensity), day length, soil type and location.

The aforementioned photographs, together with the following observations, measurements and values describe the new strawberry variety 'Shaked', unless otherwise noted, taken during the 2007–08 growing season in Hod Hasharon, Israel. The observations, measurements and values were taken from plants of 'Shaked' dug from a low-elevation nursery during May–September 2007, and planted approximately September 20 and later. Plants of the new strawberry variety 'Shaked' were grown under conditions which closely approximate those generally used in commercial practice.

Growing conditions at the nursery: Mother plants were planted in the beginning of May, in the field nursery at 2.5×2.5 m distance. Combination of overhead and drip irrigation with addition of fertilizers is used. The average day/night temperatures during the establishment of the daughter plants, between June to August, were 32° C./18° C. respectively. Runners appear beginning in June, and produced young daughter plants until mid-September. The daughter plants were then collected and planted directly in the field.

Growing conditions at the fruit production field: The bare rooted plants were rinsed, dipped in Octav (prochloraz-manganese) 2 g/l solution to avoid anthracnose, then planted in raised beds with overhead irrigation in 4 rows at 30 cm apart. Distance between plants within rows is 32 cm. During the first month, no fertilizers were added, due to the addition of 60–100 m3/hectar compost during field preparation. About 4 weeks after planting the beds were covered with silvery-black, 30 micron polyethylene. The young plants were pulled out through the pre-prepared holes. From this point on, the plants were irrigated with a drip system with a supply of additional fertilizers, as are typically used in agricultural practice. By the end of October the beds were covered with transparent, 80 micron thick polyethylene tunnels.

Maximum average daytime temperatures during the cultivation season range from about 32 to 33° C. in August, decreasing to about 16 to 20° C. in January, and increasing to about 19 to 25° C. in March. Minimum average daytime temperatures range from about 18 to 19° C. in August, decreasing to about 3 to 5° C. in January, and increasing to about 5 to 6° C. in March. (Data taken from maximum and minimum average monthly temperatures at Tel-Mond station, Sharon region, Israel, during the 1999/2000, 2000/2001, and 2001/2002 growing seasons.)

During winter in Israel, most days have full sunlight; on average, there are only 82 rainy days from August to June, producing about 620 mm precipitation. The commercial fields were not treated with growth regulators, and were regularly irrigated and fertilized according to need during fruit production.

Yield observations and fruit quality characteristics are averaged from 3 years of data collected from the 2005/6 through 2007/8 growing seasons. Flower measurements and characteristics are from secondary flowers unless otherwise noted. Fruit characteristics and measurements are from secondary fruit unless otherwise noted.

Quantified measurements are expressed as an average of measurements taken from a number of individual plants of the new variety. The measurements of any individual plant or plant part of the new variety may vary from the stated average.

Color references are made to The Royal Horticultural Society Colour Chart, except where general colors of ordinary significance are used. Color values were taken under daylight conditions at approximately noon at Bet Dagan, Israel. The approximate age of the observed plants is 1 to 10 months.

The following is a detailed botanical description of fruit, plant, stolon, foliage, fruiting truss, flower and pest/disease characteristics of the new strawberry 'Shaked'.

Fruit:

*Color of mature fruit.*—Dark red RHS 46 B.
*Color of internal flesh.*—Red RHS 46 B, red RHS 43A, and white RHS 155B.
*Length.*—52–60 mm.
*Width.*—34–40 mm.
*Ratio length/width.*—Longer than broad.
*Calyx diameter.*—33–35 mm.
*Average weight.*—25 grams.
*Achene color.*—Predominantly dark red, between RHS 45 A and RHS 45 B.
*Number of achenes per berry.*—220–320.
*Weight of* 1000 *achenes.*—0.5 gram.
*Achene size.*—Average 1.1 mm.
*Marketable yield* (*gm/plant*).—About 850 grams.
*Fruit size.*—Medium.
*Predominant shape.*—Conical.
*Difference in shapes between primary and secondary fruit.*—Slight.
*Band without achenes.*—Narrow.
*Unevenness of surface.*—Weak.
*Evenness of color.*—Even.
*Glossiness.*—Strong.
*Insertion of achenes.*—Above the surface.
*Insertion of calyx.*—Level.
*Attitude of the calyx.*—Reflexed.
*Size of calyx in relation to fruit diameter.*—Same size.
*Adherence of calyx.*—Strong.
*Firmness of flesh.*—Medium.

*Hollow center expression.*—Weak.
*Flavor.*—Excellent.
*Soluble solids* (% *brix*).—7.5–9.5.
*Time of first flowering.*—Medium, from the beginning of November.
*Time of first harvesting.*—Medium, from the beginning of December.
*Harvest period.*—November to June.
*Type of bearing.*—Partially remontant.

Plant:
*Height.*—Average 17.4 cm (in March).
*Spread.*—Average 40 cm (in March).
*Size.*—Medium.
*Habit.*—Flat globose.
*Density.*—Medium.
*Vigor.*—Medium, more vigorous than 'Tamar' (U.S. Plant Pat. No. 11,135).

Stolon:
*Average number per plant.*—Many to very many, ranging from 100 to 1000 in Israel in summer.
*Fruiting field.*—Medium.
*Color.*—Yellow green 144 C.
*Anthocyanin intensity.*—Strong.
*Diameter.*—4–5 mm.
*Length.*—10–60 cm.
*Pubescence.*—Medium to strong.

Foliage:
*Foliage.*—Color of upper surface green 147 A. Color of under side grey-green, between RHS 147 B and RHS 147 C. Shape in cross section flat. Interveinal blistering weak. Glossiness medium. Number of leaflets sometimes more than three.
*Terminal leaflet.*—Length 60–75 mm. Width 60–65 mm. Length/width ratio slightly longer than broad. Serrations/leaf average 19. Size small–medium. Shape of base rounded. Shape of teeth obtuse.
*Petiole.*—Length 9–14 cm. Diameter about 3 mm. Petiolule length 5–7 mm. Pubescence strong. Attitude of hairs outwards.
*Stipule.*—Length about 12 mm. Width about 7 mm. Anthocyanin coloration weak. Color yellow green 144 D.

Fruiting truss:
*Length.*—About 11 cm.
*Position relative to foliage.*—Above.
*Pubescence.*—Medium to strong.
*Anthocyanin intensity.*—None.
*Attitude at first pick.*—Prostrate.

Flower:
*Petal color.*—Mature (upper) white RHS 155 B. Mature (lower) white RHS 155 B.
*Petal shape.*—Overall rounded. Apex rounded. Base rounded.
*Petal length.*—13–15 mm.
*Petal width.*—15–16 mm.
*Petal length/width ratio.*—Slightly broader than long.
*Number of petals/flower.*—5 sometimes 6 or 7.
*Sepals color.*—Mature (upper) green 137 B. Mature (lower) green 138 B.
*Sepal shape.*—Overall acute. Apex truncate.
*Sepal length.*—10–11 mm.
*Sepal width.*—About 5 mm.
*Sepal length/width ratio.*—Longer than broad.
*Number of sepals/flower.*—10 sometimes 11 or 12.
*Corolla diameter.*—33–35 mm.
*Size of calyx relative to corolla.*—Same size.
*Size of inner calyx relative to outer calyx.*—Same size.
*Relative position of petals.*—Overlapping.

Pest and disease reactions:
*Powdery mildew.*—Moderately tolerant (field tolerance).

We claim:

1. A new and distinct strawberry plant named 'Shaked', as herein described and illustrated.

* * * * *